US 6,659,613 B2

(12) United States Patent
Applegate et al.

(10) Patent No.: US 6,659,613 B2
(45) Date of Patent: Dec. 9, 2003

(54) METHODS AND SYSTEMS FOR MEASURING LOCAL SCATTERING AND ABERRATION PROPERTIES OF OPTICAL MEDIA

(75) Inventors: Raymond A. Applegate, San Antonio, TX (US); Larry N. Thibos, Bloomington, IN (US)

(73) Assignees: Board of Regents, The University of Texas System, Austin, TX (US); Advanced Research and Technology Institute, Indianapolis, IN (US)

( * ) Notice: Subject to any disclaimer, the term of this patent is extended or adjusted under 35 U.S.C. 154(b) by 0 days.

(21) Appl. No.: 09/818,996

(22) Filed: Mar. 27, 2001

(65) Prior Publication Data

US 2002/0097376 A1 Jul. 25, 2002

Related U.S. Application Data

(60) Provisional application No. 60/192,173, filed on Mar. 27, 2000.

(51) Int. Cl.⁷ .................................................. A61B 3/10
(52) U.S. Cl. ...................................................... 351/221
(58) Field of Search .................................. 351/205, 211, 351/213–215, 221, 246; 356/337, 237.1, 239.1; 606/4–6; 607/88, 89; 382/279

(56) References Cited

U.S. PATENT DOCUMENTS

| | | | |
|---|---|---|---|
| 5,579,063 A | * 11/1996 | Magnante et al. | 351/211 |
| 5,777,719 A | * 7/1998 | Williams et al. | 351/212 |
| 6,086,204 A | * 7/2000 | Magnante | 351/212 |
| 6,199,986 B1 | * 3/2001 | Williams et al. | 351/221 |
| 6,273,566 B1 | * 8/2001 | Kobayashi et al. | 351/221 |
| 6,429,415 B1 | * 8/2002 | Rhoads | 250/201.9 |
| 6,439,720 B1 | * 8/2002 | Graves et al. | 351/211 |

OTHER PUBLICATIONS

"Deconvolution from wave–front sensing: a new technique for compensating □□turbulence–degraded images," J. Primot et. al., J. Opt. Soc. Am. A Vol 7 No9, □□p 1598.*
Liang and Williams, "Aberrations and retinal image quality of the normal human eye," J. Opt. Soc. Am. A., 14(11):2873–2883, 1997.

(List continued on next page.)

Primary Examiner—Marvin M. Lateef
Assistant Examiner—John R Sanders
(74) Attorney, Agent, or Firm—Fulbright & Jaworski, LLP

(57) ABSTRACT

Methods, systems, and media relating the display of scattering and/or absorption characteristics of an optical medium. For scattering measurements, a Hartmann-Shack calibration image of a measurement system is acquired to define a first plurality of point spread functions. A Hartmann-Shack test image of the medium is acquired to define a second plurality of point spread functions. A shift is determined between the test image and the calibration image. A point spread of each of the second plurality of point spread functions is measured, each of the second plurality of point spread functions including a component due to optical aberration of the medium and a component due to scatter. The component due to optical aberration is determined using the shift. The component due to optical aberration is deconvolved to determine the component due to scatter. A display of the local scattering characteristics is generated using the component due to scatter. For absorption measurements, a plurality of spot intensity measurements are acquired of a medium, each spot intensity measurement including a component due to reflectivity and a component due to absorption. The component due to reflectivity is determined, and the component due to absorption is determined.

20 Claims, 11 Drawing Sheets

OTHER PUBLICATIONS

Liang et al., "Objective measurement of wave aberrations of the human eye with the use of a Hartmann–Shack wave-front sensor," *J. Opt. Soc. Am. A.*, 11(7):1949–1957, 1994.

Liang et al., "Supernormal vision and high–resolution retinal imaging through adaptive optics," *J. Opt. Soc. Am. A.*, 14(11):2884–2892, 1997.

Pratt, Digital Image Processing, Second Edition, Wiley Interscience, 1991, Chapter 12.

Roorda and Williams, "The arrangement of the three cone classes in the living human eye," *Nature*, 397:520–522, 1999.

Salmon et al., "Comparison of the eye's wave–front aberration measured psychophysically and with the Shack–Hartmann wave–front sensor," *J. Opt. Soc. Am. A.*, 15(9):2457–2465, 1998.

Smith, "Image Evaluation," Modern Optical Engineering, Second Edition, McGraw–Hill, 1990, Chapter 11.

Thibos and Hong, "Clinical Applications of the Shack–Hartmann Aberrometer," *Optometry and Vision Science*, 76(12):817–825, 1999.

\* cited by examiner

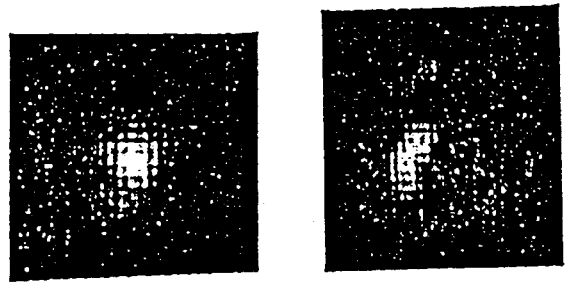
FIG. 5C
FIG. 5D
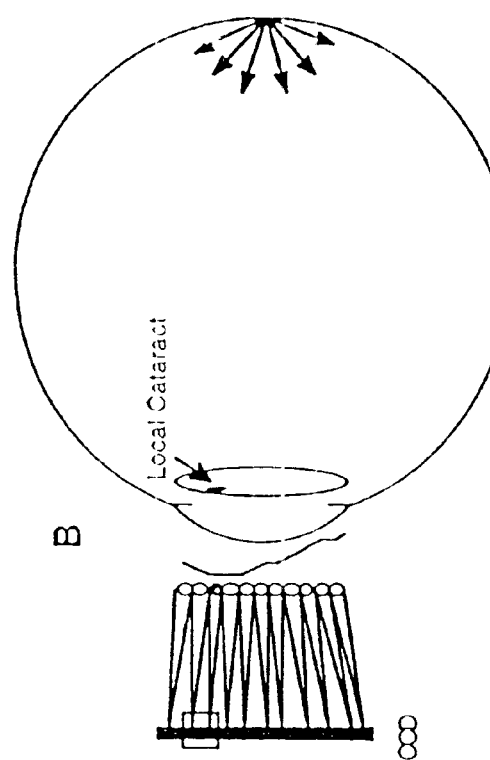
FIG. 5B
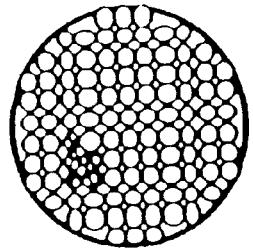
FIG. 5A

FIG. 6
FIG. 7
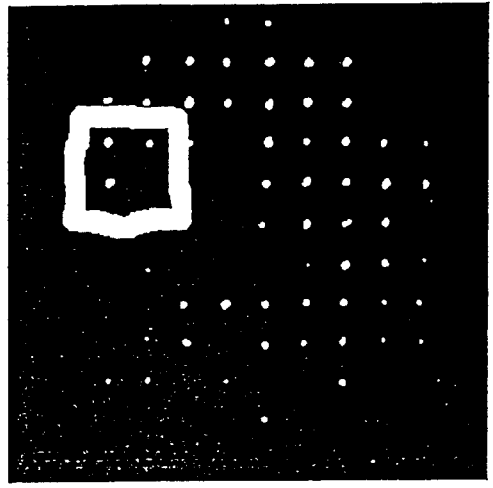
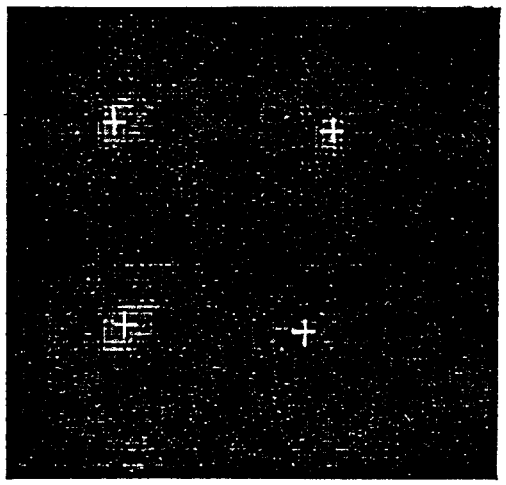
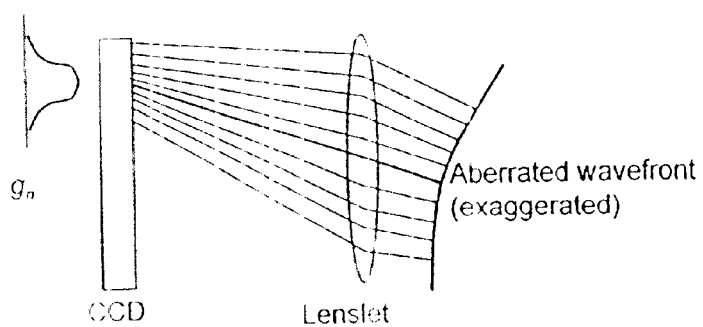
FIG. 8 x h y

METHODS AND SYSTEMS FOR MEASURING LOCAL SCATTERING AND ABERRATION PROPERTIES OF OPTICAL MEDIA

This application claims priority to provisional patent application Serial No. 60/192,173 filed Mar. 27, 2000, entitled, "Methods and Systems for Measuring Local Scattering and Aberration Properties of Optical Media" by Raymond A. Applegate and Larry N. Thibos. The entire text of the above-referenced disclosure is specifically incorporated by reference herein without disclaimer.

The government may own rights in the present invention pursuant to grant number R01-EY-05109 and/or R01-EY-08520 from the National Eye Institute.

BACKGROUND OF THE INVENTION

1. Field of the Invention

The present invention relates generally to the fields of optical measurements. More particularly, it concerns methods and systems for measuring spatially-resolved scattering of an optical medium, including the eye.

2. Description of Related Art

Because optical media, including the eye, may include several types of defects that negatively affect image quality, several instruments have been developed in an attempt to measure and correct such defects. One such instrument is the spatially-resolved optometer. The idea of a spatially-resolved optometer originated in the early $19^{th}$ century with Thomas Young, who employed a double pinhole technique to sample a wavefront entering the eye at two locations. Using such an instrument, one may obtain a gross measure of the refractive state of the eye, but one may not discriminate between defocus, astigmatism, and higher order aberrations. Also, the Thomas Young optometer requires subjective judgments by the observer, which introduce sources of uncontrolled variability. Modern clinical optometers (e.g. auto refractors) have the advantage of objectivity, but still suffer from limitations similar to those suffered by the optometer of Thomas Young.

Recent technological advances in the field of visual optics research have made it possible to quickly obtain an objective, high-resolution map of the refractive state of the eye at several hundred sample points within the eye's pupil. From this matrix of sample points, it is possible to derive a wavefront aberration function of the eye, which is a fundamental description of the eye's optical characteristics from which traditional measures of refractive error (e.g. the degree of myopia, hyperopia, or astigmatism) may be derived. Furthermore, the wavefront aberration function may be used to compute metrics of retinal image quality, such as the point spread function or the optical transfer function. For at least these reasons, the wavefront aberration function is a richer and more useful description of the optical properties of the eye than is obtained by conventional optometers.

Currently available methods for measuring the eye's wavefront aberration functions fall into two broad categories—subjective and objective. However, each of these methods share a common principle: the eye's pupil is sub-divided into a number of sub-apertures, the rays passing through these sub-apertures are isolated, and their direction of propagation measured. Aberrations are then quantified by the deviation of these isolated rays from the trace of corresponding rays in an aberration-free system. In effect, a beam of light passing through the eye's pupil is spatially resolved into a number of smaller beams which are independently measured in order to gain detailed characterization of the refractive anomalies of an eye.

Subjective methods for measuring ray aberrations all require that the subject judge the apparent visual direction of discrete points in the retinal image that result from rays passing through specific points in the pupil plane. In the aberroscope method, for example, a grid is placed over the pupil, and the eye is deliberately defocused in order to produce a blur circle that replicates the shape of the pupil, including the grid of opaque lines. Since each intersection of grid lines corresponds to a specific pupil location, distortions seen in the retinal shadows of the grid may be used to infer the directions of identified rays as they leave the eye pupil and eventually intersect the retina. In effect, the subjective aberroscope is a ray tracing device that allows the simultaneous monitoring of multiple rays as they pass through known pupil locations. The subject's task in this case is to estimate the apparent visual direction of each point on the grid by perceptually interpreting the retinal stimulus as if it were the conventional image of a real object formed by the eye's optical system.

An alternative subjective approach developed originally by Smirnov uses a single pinhole aperture to isolate a narrow bundle of rays from an axial point source as they pass through a known location in the eye's pupil. In an aberrated eye, the retinal intersection of this ray bundle will not coincide with the axial retinal image of a reference point source. The subject will therefore perceive the test and reference point sources as having different visual directions. To nullify this difference in visual direction, the subject displaces the test light until it appears to coincide with the reference light. In this way, the ray aberration is transferred from image space to object space where it may be measured quantitatively. Unfortunately, the method of subjective magnitude estimation is inherently unreliable, and the nulling method used in the Smirnov technique is very time consuming. In short, both methods place an excessive demand on the subject, which makes both techniques unsuitable for routine use with patients in a clinical setting.

In response to the problems of subjective techniques, certain objective methods for measuring wavefront aberration functions of the eye have been developed. One method is an objective aberroscope which uses a fundus camera to record an image of a distorted grid on the retina. One of the limitations of the objective aberroscope is that the eye's optical system serves as the objective lens for the fundus camera. Consequently, even for eyes with normal levels of aberration, the eye's imaging quality limits the minimum useable spacing between grid lines in the pupil plane to about one millimeter, thus limiting the resolution with which the eye's aberrations may be specified. For the same reason, a highly aberrated eye may not yield an image of sufficient quality to allow reliable measurements of the aberration function with such a device.

Both of these problems with the aberroscope method are avoided by another objective method, the Hartmann-Shack wavefront sensor, which characterizes the eye's aberration in object space. Developed for astronomical applications and adapted recently for the eye, this wavefront sensor uses an array of lenses and a video detector to measure rays of reflected light emerging from the eye. In the Hartmann-Shack method, a narrow beam of light is directed into the eye to produce a high quality point source of light on the fundus. Light reflected from the fundus is then subdivided into a large number of ray bundles as it leaves the eye. This is achieved by placing an array of tiny lenses in a plane conjugate with the eye's pupil plane. A video detector (CCD) located at the focal plane of the lenslet array thus records an array of point images, one for each lens in the array. For an eye free of defocus and aberrations, all of the exiting ray bundles would be parallel, and therefore the CCD would record an array of point images with the same imagery as the lenslet ray. Deviations from this geometry may therefore be attributed to aberrations in the exiting beam. Given that high density lenslet arrays are now available commercially from, e.g., Adaptive Optics Associates (Cambridge, Mass.), the Hartmann-Shack method for measuring the wave aberration function in human eyes is emerging as an important method for fast, objective high spatial resolution in the pupil plane.

Although the above techniques have exhibited at least a degree of usefulness for determining spatially-resolved aberration functions of the eye, those methods ignore information relating to localized scatter (and absorption) within the eye. In particular, current methods utilizing Hartmann-Shack measurements concentrate upon the deviation of spot images within a Hartmann-Shack image from that of an ideal geometrical array rather than concentrating upon scattering and absorption information present within those images. Because a wide variety of optical imperfections may cause scattering of light, absorption of light, or aberrations too fine to be resolved by a wavefront sensor, it would be advantageous to provide for the ability to measure local scattering and absorption within an optical medium, including the eye. More particularly, abnormalities including, but not limited to, abnormalities of the tear film, corneal scars, opacities, vacuoles, edema, foreign bodies in the anterior or vitreal chambers, cataracts, gradients in refractive index, structural abnormalities of the crystalline lens, drusen, pigmentation of the neural retina, or optical dirty contact lenses or spectacle lenses may all serve as a source of scatter and/or absorption that may be identified and/or localized if one has the ability to effectively measure local scatter and/or absorption within a media.

SUMMARY OF THE INVENTION

In one respect, the invention is a method for measuring scattering of an optical medium. A plurality of point spread functions of the medium is acquired, each point spread function including a component due to optical aberration of the medium and a component due to scatter. The component due to optical aberration is determined, and the component due to scatter is determined.

In other respects, the acquiring may include acquiring a Hartmann-Shack image. The method may also include generating a display of the scattering of the medium. The medium may include an eye. The method may also include identifying a defect of the eye using the component due to scatter, the defect contributing to local scattering. Identification of the defect may occur before or after laser eye surgery. The defect may include a cataract. The defect may include an abnormality of a tear film, a corneal scar, a vacuole, edema, a foreign body, an abnormality of a lens, an abnormality of the vitreous, drusen, defective contact lenses, defective spectacle lenses, IOL, or any combination thereof. The method may also include treating the defect. Any treatment methodology known in the art may be utilized for such treatment.

In another respect, the invention is a method for displaying local scattering characteristics of an optical medium. A Hartmann-Shack calibration image of a measurement system is acquired to define a first plurality of point spread functions. A Hartmann-Shack test image of the medium is acquired to define a second plurality of point spread functions. A shift between the test image and the calibration image is determined. A point spread of each of the second plurality of point spread functions is measured, each of the second plurality of point spread functions including a component due to optical aberration of the medium and a component due to scatter. The component due to optical aberration is determined using the shift. The component due to optical aberration is deconvolved to determine the component due to scatter. A display of the local scattering characteristics is generated using the component due to scatter.

In other respects, the medium may include an eye. The method may also include identifying a defect of the eye using the component due to scatter, the defect contributing to local scattering. Identification of the defect may occur before or after laser eye surgery. The defect may include a cataract. The defect may include an abnormality of a tear film, a corneal scar, a vacuole, edema, a foreign body, an abnormality of a lens, an abnormality of the vitreous, drusen, defective contact lenses, defective spectacle lenses, IOL, or any combination thereof. The method may also include treating the defect.

In another respect, the invention is a system for measuring scattering of an optical medium, including an imaging device, a memory, and a microprocessor. The imaging device is configured to acquire a plurality of point spread functions of the medium, each point spread function including a component due to optical aberration of the medium and a component due to scatter. The memory is configured to store information corresponding to the plurality of point spread functions. The microprocessor is in communication with the memory and is configured to perform instructions using the information. The instructions include: determining the component due to optical aberration and determining the component due to scatter.

In other respects, the imaging device may include a Hartmann-Shack wavefront sensor. Each point spread function may also include a component due to optical aberration of a measurement system, and the instructions may also include determining the component due to optical aberration of the measurement system. The instructions may also include instructions for generating a display of the scattering of the medium. The medium may include an eye. The instructions may also include identifying a defect of the eye using the component due to scatter, the defect contributing to local scattering. Identification of the defect may occur before or after laser eye surgery. The defect may include a cataract. The defect may include an abnormality of a tear film, a corneal scar, a vacuole, edema, a foreign body, an abnormality of a lens, an abnormality of the vitreous, drusen, defective contact lenses, defective spectacle lenses, IOL, or any combination thereof.

In another respect, the invention is a computer readable media containing program instructions for measuring scattering of an optical medium. The computer readable media includes instructions for measuring a point spread of each of a plurality of point spread functions, each of the point spread functions including a component due to optical aberration of the medium and a component due to scatter. The media includes instructions for determining the component due to optical aberration and instructions for determining the component due to scatter.

In other respects, each point spread function may also include a component due to optical aberration of a measurement system, and the media may include instructions for determining the component due to optical aberration of the measurement system. The instructions for determining the component due to scatter may include instructions for deconvolving the components due to optical aberration of the medium and of the measurement system from the component due to scatter. The media may also include instructions for generating a display of the scattering of the medium. The medium may include an eye. The media may also include instructions for identifying a defect of the eye using the component due to scatter, the defect contributing to local scattering. Identification of the defect may occur before or after laser eye surgery. The defect may include a cataract. The defect may include an abnormality of a tear film, a corneal scar, a vacuole, edema, a foreign body, an abnormality of a lens, an abnormality of the vitreous, drusen, defective contact lenses, defective spectacle lenses, IOL, or any combination thereof.

In another respect, the invention is a method for identifying a defect of an eye. A plurality of point spread functions of the eye are acquired, each point spread function including a component due to optical aberration of the medium and a component due to scatter. The component due to optical aberration is determined. The component due to scatter is determined, and the defect is identified using the component due to scatter.

In other respects, the method may also include treating the defect. Any treatment methodology known in the art may be utilized for such treatment.

In another respect, the invention is a method for identifying a defect of an eye. A Hartmann-Shack calibration image of a measurement system is acquired to define a first plurality of point spread functions. A Hartmann-Shack image of the eye is acquired to define a second plurality of point spread functions. A shift between the image of the eye and the calibration image is determined. A point spread of each of the second plurality of point spread functions is measured, each of second plurality of point spread functions including a component due to optical aberration of the medium and a component due to scatter. The component due to optical aberration is determined using the shift. The component due to optical aberration is deconvolved to determine the component due to scatter, and the defect is identified using the component due to scatter.

In other respects, the method may also include treating the defect. Any treatment methodology known in the art may be utilized for such treatment.

In another respect, the invention is a method for measuring absorption of an optical medium. A plurality of spot intensity measurements of the medium are acquired, each spot intensity measurement including a component due to reflectivity and a component due to absorption. The component due to reflectivity is determined, and the component due to absorption is determined.

In other respects, the acquiring may include acquiring a Hartmann-Shack image. The method may also include generating a display of the absorption of the medium. The medium may include an eye. The method may also include identifying a defect of the eye using the component due to absorption, the defect contributing to local scattering. Identification of the defect may occur before or after laser eye surgery. The defect may include a cataract. The method may also include treating the defect. Any treatment methodology known in the art may be utilized for such treatment. The determining the component due to reflectivity may include determining a Stiles-Crawford function.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 5A–5D illustrate Hartmann-Shack wavefront sensing in accordance with the present disclosure.

FIG. 5A shows a Hartmann-Shack lenslet array image.

FIG. 5B shows a schematic of a Hartmann-Shack system imaging an eye that includes a cataract.

FIGS. 5C and 5D show two neighboring lenslet images showing variations in local scattering.

FIG. 6 shows a Hartmann-Shack image of an eye with four lenslet images circled.

FIG. 7 is an enlarged view of the circled lenslet images of FIG. 6 and illustrates the variation in scatter that is being superimposed on the wavefront over very small distances. In this figure, centroids are shown by the crosses. Individual lenslets in this figure are at intervals of about 0.4 mm.

FIG. 8 illustrates the generation of a geometric point spread function due to an aberrated wavefront in accordance with the present disclosure. In this figure, a two-dimensional histogram of ray intersections is computed and provides an estimate of $g_n$ for an individual lenslet.

FIG. 12 shows a Hartmann-Shack image. FIG. 13 shows a corresponding local scatter map generated from FIG. 12.

FIG. 17 (y) is a simulation of a lenslet image consisting of three components: the point spread due to instrumentation, the point spread due to local aberrations, and the point spread due to scatter. FIG. 16 (h) shows the local point spread due to instrumentation and aberration. FIG. 15 (x) shows the exact deconvolution of h from y and represents the portion of y attributable to scatter.

DESCRIPTION OF ILLUSTRATIVE EMBODIMENTS

Methods and systems practiced according to techniques disclosed herein offer several significant advantages. The present disclosure provides for the ability to spatially resolve local scattering and absorption characteristics of optical media, including the eye. That ability allows for the identification (including localization) of a wide variety of defects that act as scattering and/or absorption sources within the media. Defects that may be identified within the eye include, but are not limited to, abnormalities of the tear film, corneal scars, opacities, vacuoles, edema, foreign bodies in the anterior or vitreal chambers, cataracts, gradients in refractive index, structural abnormalities of the crystalline lens, drusen, pigmentation of the neural retina, and optically dirty, malformed, or defective contact lenses or spectacle lenses. Defects that may be identified within other optical media include, but are not limited to imperfections in anti-reflective optical coatings on lenses, scratches or surface imperfections of polished or molded lenses, scattering and absorptive elements within the media, and imbedded imperfections in molded lenses.

As will be understood by those of skill in the art with the benefit of this disclosure, there are several applications that can take advantage of the ability of the technology disclosed herein to identify a wide variety of defects. For instance, in one non-limiting example, one may employ techniques of the present invention in conjunction with pre- or post-laser eye surgery. Prior to undergoing laser eye surgery, patients typically undergo one or more evaluation exams. During these exams, the technology disclosed herein may be used to identify one or more defects or imperfections that may impact the laser surgery. Similarly, the technology disclosed herein may be used during the one or more evaluations that commonly follow laser eye surgery. During these post-operative exams, eye clinics typically measure their patients' visual acuity and evaluate how well their patients' cornea is healing. Techniques of the present invention may be used during these post-operative exams to additionally identify eye defects or imperfections.

Those having skill in the art will recognize a great number of additional applications for the technology disclosed herein—at least any application where one desires to identify optical properties, defects and/or imperfections.

Although much of the description below will refer to measurements of the eye, those having skill in the art will recognize, with the benefit of this disclosure, that this description applies equally well to any other optical media under measurement, such as but not limited to, surfaces, lenses, mirrors, combinations thereof to form an optical system, and the like.

Figure 1:
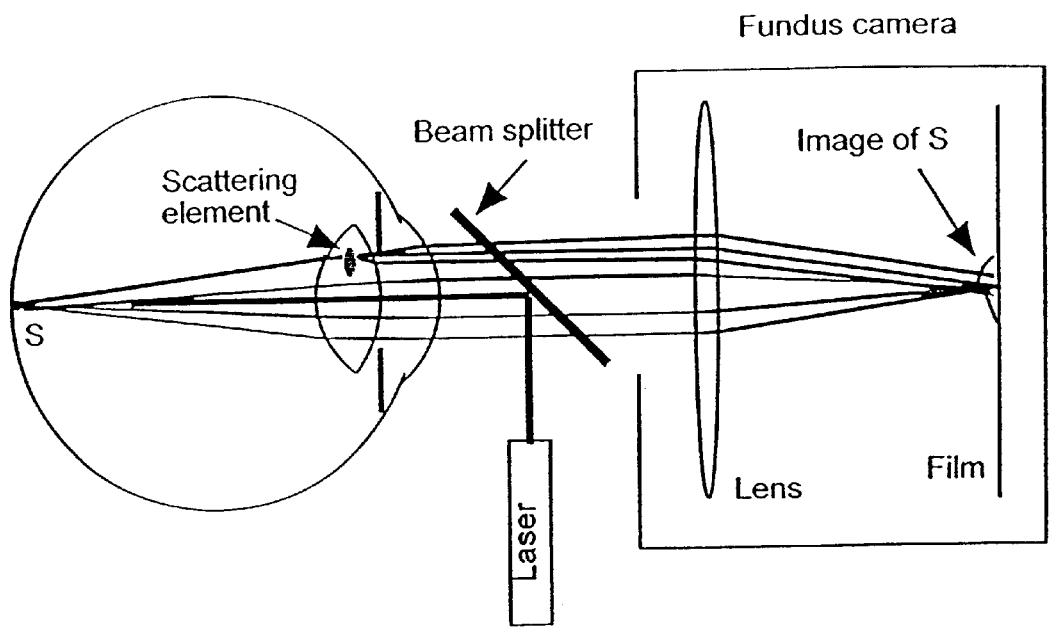
FIG. 1 is a schematic illustrating conventional fundus imaging.

Techniques disclosed herein utilize an array of sub-apertures to subdivide and localize light emerging from optical media under test (such as an eye). In one embodiment, one may subdivide and localize the light by replacing the imaging lens in a fundus camera (See FIG. 1) with an array of lenslets as shown generally by FIG. 2. The array of lenslets may be made with lenses, prisms, or other techniques suitable for dividing beams of light. Each lenslet performs at least two functions. First, each lenslet acts as a sub-aperture to isolate a portion of the beam of light exiting the eye. Second, each lenslet focuses the isolated beam onto a film plane to record an image of the source S. In another embodiment, the lenslets may focus the isolated beam onto a more elaborate measurement system such as a spectrograph. By subdividing the reflected beam of light emerging from the eye in this way, the scattered light from different parts of the pupil may be kept separate, with each lenslet forming an image using that portion of light that falls on its entrance aperture. In this way, the light may be spatially-resolved into a number of sub-beams, each of which corresponds to a particular light path through the eye. Through sub-division and localization of the light, the present disclosure allows for the acquisition of lenslet images and the ability to correlate those images with (x,y) locations of the optical media under test.

Figure 3:
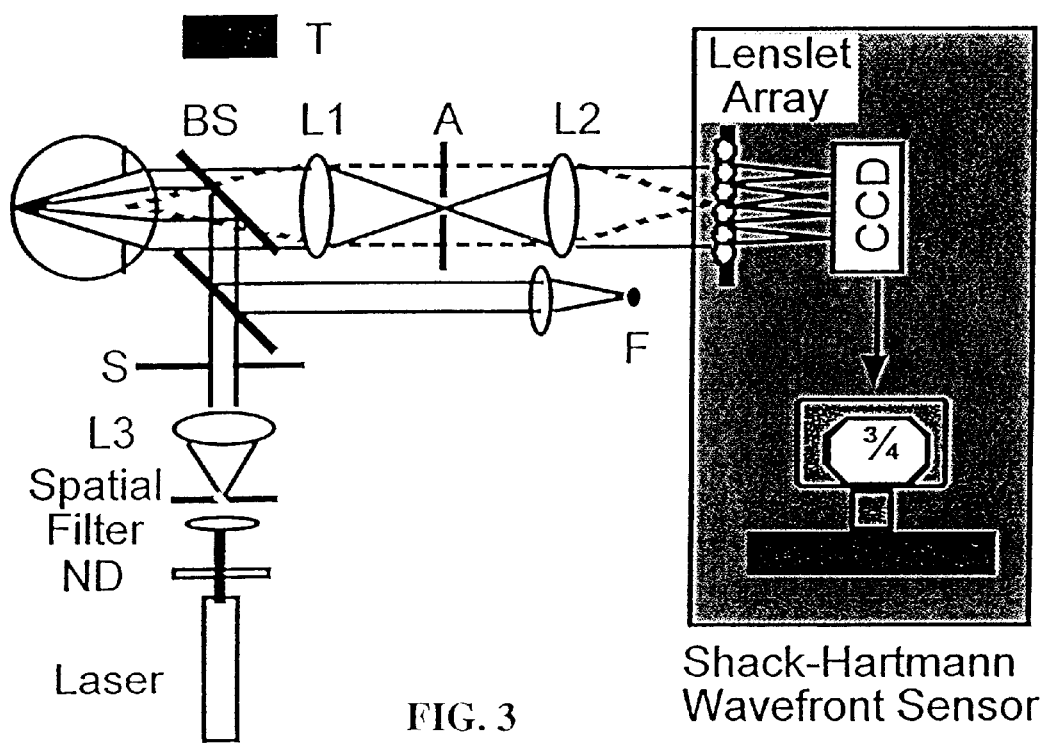
FIG. 3 is a schematic of a Hartmann-Shack wavefront sensor suitable for use with systems and methods of the present disclosure.

In one embodiment, one may use a Hartmann-Shack wavefront sensor to subdivide the light exiting an optical media. A schematic diagram of a suitable Hartmann-Shack measurement system for use with the eye is shown in FIG. 3. As illustrated, the Hartmann-Shack sensor may include a micro-lenslet array, a CCD video camera, and a computer to analyze the data images. The rest of the illustrated system performs three main functions: (1) form a point source of light on the retina that will be a source of reflected light captured by the CCD camera, (2) provide a fixation target for the observer, and (3) focus the eye's pupil plane in the plane of the lenslet array. In the illustrated embodiment, the light source may be a HeNe (about 632.8 nm) laser beam which is spatially filtered, collimated, and reduced in diameter to about 1 mm with an adjustable stop S. A confocal aperture (A) may be inserted into the system to block the corneal reflection of the incident laser beam while allowing the reflected light from the retina to pass. The micro-lenslet array may be a square matrix of lenslets with center-to-center spacing on the order of about 0.4 mm, which provides several hundred measurements of the reflected wavefront shape over a dilated pupil. Aberrations of the optical components of the measurement system itself (which will be described in more detail below) may be determined by replacing the light trap T with a mirror and expanding the adjustable stop S in order to reflect a plane wave through the system. The resulting aberration coefficients may be subtracted from experimental measurements on eyes to correct for errors introduced by the aberrometer.

Figure 4:
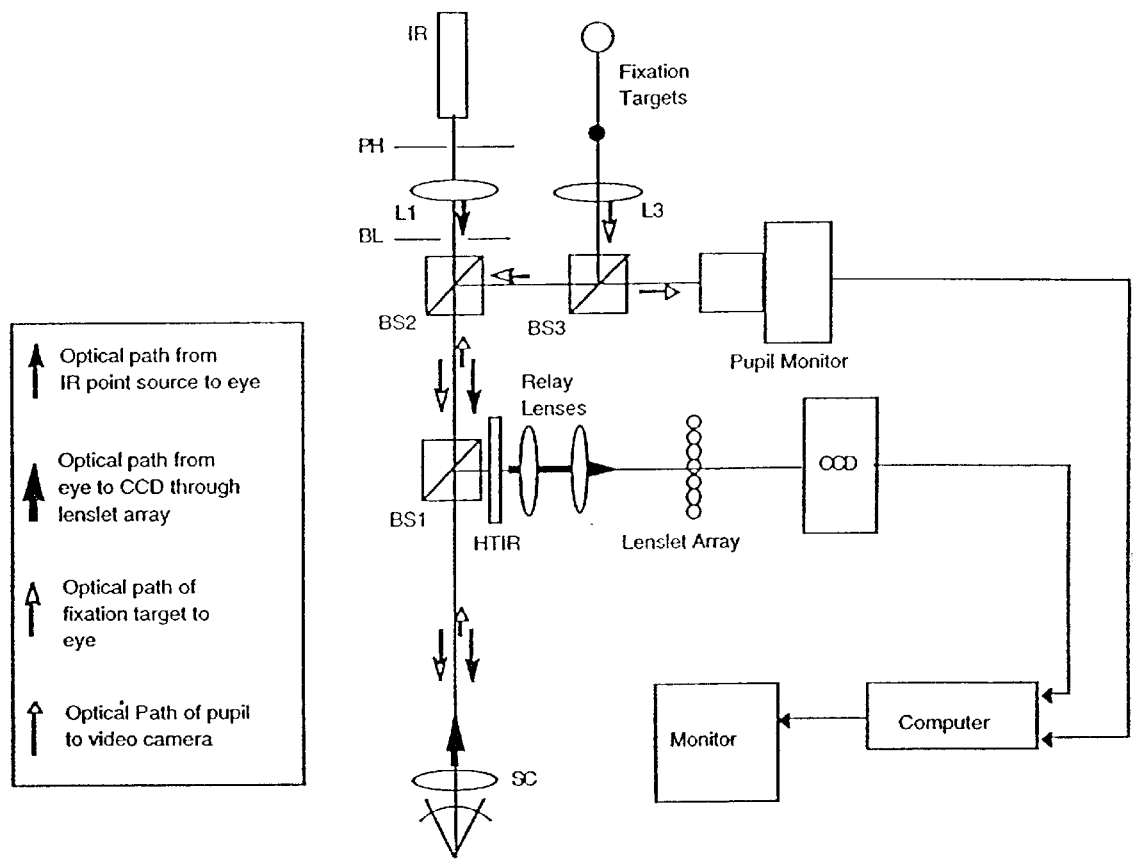
FIG. 4 is a schematic of another Hartmann-Shack wavefront sensor suitable for use with systems and methods of the present disclosure.

A schematic diagram of another suitable Hartmann-Shack measurement system is shown in FIG. 4. In this figure, an infrared diode laser (IR) may be configured to illuminate about a 50 micrometer pinhole (PH) placed about 1 focal length from lens L1. An IR laser may be preferable for patient comfort. The resulting collimated IR beam may be constrained by a circular beam limiting aperture (BL) to about 1.5 mm and passed through two beam splitters and optimal spectacle correction (SC) to enter the eye (or other optical medium) to form a point source (on the retina). A portion of the retinal point image is reflected back out of the dilated eye back through the SC and is diverted toward the Hartmann-Shack lenslet array by a polarizing beam splitter (BS1) that minimizes the specular reflection from the corneal first surface and spectacle correction. After reflection at BS1 visible stray light may be minimized by a high transmittance infrared filter (HTIR). The relay lenses form an image of the eye on the Hartmann-Shack lenslet array. The CCD is placed at the focal length of the lenslet array. Images formed by the lenslet array may be captured by the CCD and transmitted to a computer or other suitable calculating device for display, analysis and/or storage.

In FIG. 4, the line of sight may be used to align the patient to the optical axis of the instrument. Use of the line of sight, as opposed to the visual axis, ensures that the center of the eye's pupil is placed on optical axis of the instrument. Using the center of the pupil as the reference for the calculation of optical aberrations, which is standard procedure known in the art, may be accomplished by one of two ways or a combination of both. Subjective alignment may be achieved by having the subject adjust their head position until an out of focus fixation dot (located on the optical axis of the instrument) is in the center of the in focus fixation circle (also centered on the optical axis of the instrument) in the same manner that a rifle is sighted. Or, an objective alignment may be achieved by the experimenter using a magnified view of the pupil and an adjustable alignment ring centered on the optical axis of the instrument (not shown) provided by the pupil monitor and moving the subject's head until the eye's pupil is circumscribe by the alignment ring. Or the subjective method may be used to bring the subject into preliminary alignment with final alignment being performed by the experimenter using the objective method.

Figure 2:
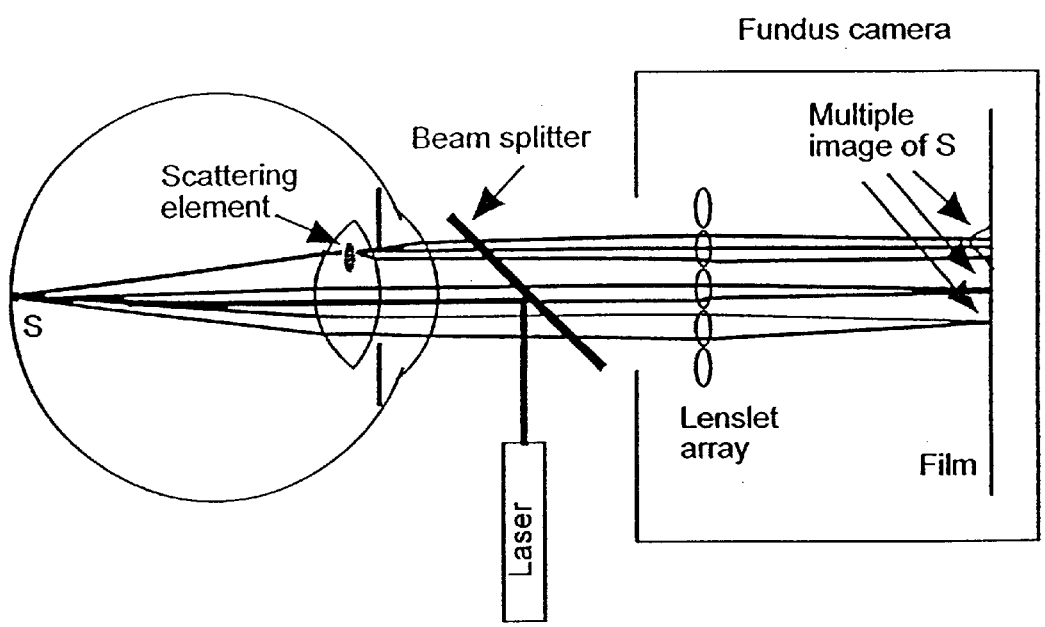
FIG. 2 is a schematic illustrating the use of an array of lenslets in accordance with the present disclosure.

The departure of an image formed on the film of FIG. 2 or upon the CCD of FIGS. 3 or 4 from a diffraction-limited point image may arise from at least three possible causes: (1) optical aberrations within the measurement system, (2) aberrations in the patient's eye, and (3) scatter (i.e. microaberrations on a spatial scale less than the diameter of an individual lenslet) from the patient's eye.

The contribution of causes #1 and #2 may be measured by conventional Hartmann-Shack wavefront sensor methods, as is known in the art. Because the final image of source S is equal to the convolution of the point-spread functions due to each of the three sources identified above, the mathematical process of deconvolution may be used to recover the scattered image from cause #3 given quantitative measurements of spread due to the other sources. In this way a quantitative, spatially-resolved measure of the light scattering properties of each isolated path through the eye's optical system may be determined and may provide for the advantages mentioned above.

FIGS. 5–7 illustrate the departure of an image due to cause #3—scatter. In FIGS. 5A–5D, there is shown a portion of wavefront sensing system measuring local scatter (and absorption) of an eye in accordance with the present disclosure. FIG. 5A shows the eye's pupil subdivided by lenslet array that spatially subdivides and samples the optics of the eye. FIG. 5B is a simplified schematic of a Hartmann-Shack system (or other suitable system) such as those better-illustrated in FIGS. 2–4. In FIG. 5B, a point source is generated on the retina. Light from the point source passes through the eye's optics and forms a distorted wavefront (distorted for reasons such as #1–#3 listed above) that is dissected by the lenslet array of the system. In the illustration, scattering distortions may be due, at least in part, to the presence of the illustrated cataract. The image location in the plane of the CCD formed by each lenslet depends on the local slope of the wavefront as it enters the lenslet. The displacement of the image location from calibrated positions allows the wavefront to be reconstructed, as is known in the art, to determine the amount of distortion caused by reasons #1 and #2 listed above. If there is a local scattering component in the wavefront the point spread of the affected lenslets (the lenslets that are darkened in FIG. 5A) will be more spread than for unaffected lenslets. FIGS. 5C and 5D are images showing the large variations in image spread due, at least in part, to local scattering. FIGS. 6 and 7 also show the departure of an image due to scatter. In FIGS. 5–7, this departure of images may be quantified to determine local scattering characteristics which may, in turn, lead to identification and local quantification of cataracts and other optical defects. The quantification process is described in more detail directly below.

The point spread of each lenslet image from a patient (or from an inanimate object) measurement may be thought of as the convolution of three point spread functions: (1) the local (over the aperture of the lenslet) point spread of the measurement system (to correct for variations in calibrated lenslet point spread functions); (2) the point spread due to the local optical aberration of the object being measured; and (3) the point spread due to local scatter of the object. For general discussion of statistical optics, one may look to, for example, Goodman, J. W. (1985) Statistical Optics, New York, John Wile & Sons. The contribution of local scatter may be calculated by deconvolving the local point spread function due to instrumentation and local aberration, leaving the contribution from scatter. The magnitude of the local scatter may be quantified using the variance of the scatter, the root-mean-square (RMS) point spread function, or other methods known by those having skill in the art.

For a given lenslet n, the point spread function of a calibration image (point spread function #1 above) may be denoted $f_n$, and the point spread function of the local optical aberration (point spread function #2 above) may be denoted $g_n$. One may compute $h_n$ as the two-dimensional linear convolution of $f_n$ with $g_n$ as shown in Equation (1).

$$h_n = f_n * g_n \quad (1)$$

One may obtain $f_n$ directly from a calibration image as is known in the art and may compute $g_n$ as the geometric point spread function from the local optical aberration, as is also known in the art. In this regard, one may look to references such as Liang et al., "Objective measurement of wave aberrations of the human eye with the use of a Hartmann-Shack wave-front sensor," vol. 11, no. 7, J. Opt. Soc. Am. A, July 1994, pp. 1949 –1957; Liang et al., "Supernormal vision and high-resolution retinal imaging through adaptive optics," vol. 14, no. 11, J. Opt. Soc. Am. A, November 1997, pp. 2884–2892; and U.S. Pat. No. 5,777,719; all three of which are hereby incorporated by reference. In one embodiment, a method described in Smith, Modem Optical Engineering, Second Edition, McGraw-Hill, 1990, Chapter 11, which is incorporated herein by reference, may be used to calculate geometric point spread function $g_n$ by tracing a large number of rays from the local optical aberration wavefront and computing the histogram of the image plane intersections as illustrated in FIG. 8. Once calculated, the result may be used to calculate $h_n$. In another embodiment, a method described in Gaskill, J. D. (1978), Linear Systems, Fourier Transforms, and Optics, New York, John Wiley & Sons, which is incorporated herein by reference, may be used to calculate geometric point spread function $g_n$ by computing the squared magnitude of the Fourier transform of the pupil function representing the local aberration.

Figure 9:
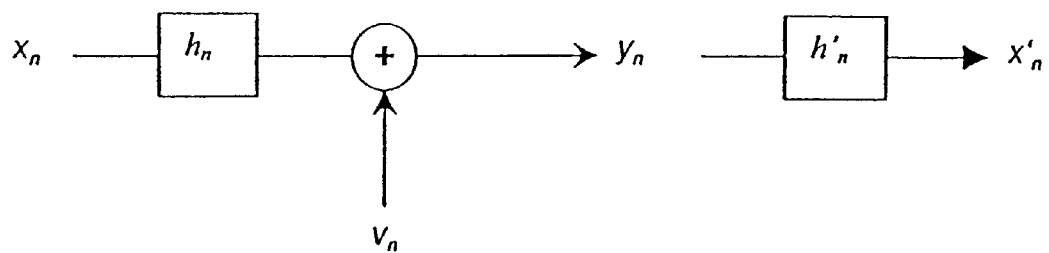
FIG. 9 is a schematic of a signal processing model of lenslet image $y_n$ formed as the sum of random noise $v_n$ and the convolution of scatter $x_n$ with point spread function $h_n$ in accordance with the present disclosure. The restoration (deconvolution) filter $h_n$ provides an optimal linear least squares estimate $x'_n$ of $x_n$.

To isolate the contribution of scatter, one must deconvolve $h_n$ from the measured point spread function so as to leave only the scatter component. A standard model employed to derive an optimal linear least-squares deconvolution operation (e.g., see Pratt, Digital Image Processing, Second Edition, Wiley Interscience, 1991, Chapter 12, which is incorporated herein by reference) is illustrated in FIG. 9. In FIG. 9, $y_n$ is the observed lenslet image, $x_n$ is the scatter for which a quantitative determination is desired, $h_n$ is the combined point spread function computed above, $v_n$ is additive random noise, $h'_n$ is the optimal deconvolution filter, and $x'_n$ is the optimal estimate of $x_n$.

It can be shown (see Pratt) that the Fourier transform of the optimal linear least squares deconvolution filter $H'_R$ (also known as a Wiener filter) is given by Equation (2) where $H_n$ is the Fourier transform of the point spread function $h_n$, $S_v$ is the power spectral density of the noise, and $S_x$ is the power spectral density of the scatter.

$$H'_R = \frac{1}{H_n} \times \frac{|H_n|^2}{|H_n|^2 + S_v/S_x} \quad (2)$$

While it is possible to estimate $S_v$ from a sequence of calibration images, $S_x$ is unknown. Thus, one may use the real-world approximation to (2) given in Equation (3) where the constant k may be empirically determined from sequences of exams (see Gonzalez and Woods, Digital Image Processing, Addison Wesley, 1992 or Russ, The Image Processing Handbook, second edition, CRC Press, 1994, both of which are hereby incorporated by reference).

$$H'_R = \frac{1}{H_n} \times \frac{|H_n|^2}{|H_n|^2 + k} \quad (3)$$

The Fourier transform of the scatter $X'_n$ may then be computed as the point-wise product of Fourier transform of the lenslet image $Y_n$ with $H'_R$, and the estimate of the scatter $x'_n$ may then be computed as its inverse Fourier transform. The indicated forward and inverse Fourier transforms may be computed using two-dimensional Fast Fourier Transforms (FFTs) with appropriate zero padding, as is known in the art. Finally, the variance for the scatter may be computed in the usual manner as shown in Equation (4) for all M points in a local region of the lenslet n.

$$m_x = \frac{1}{M} \sum_{i=0}^{M-1} x'_n(i) \quad (4)$$

$$\text{var} x'_n = \frac{1}{M} \sum_{i=0}^{M-1} [x'_n(i) - m_x]^2$$

Figure 10:
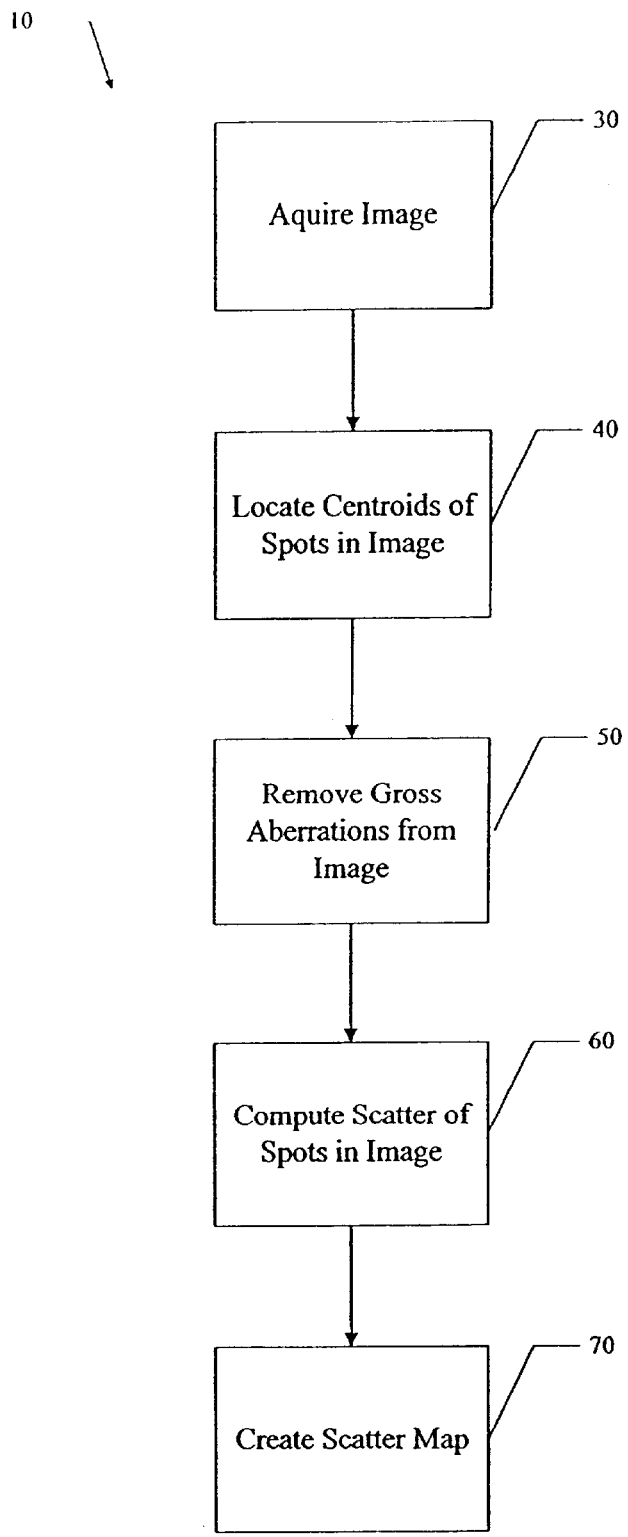
FIG. 10 is a flow chart illustrating a method for measuring local scattering of an optical medium according to the present disclosure.
Figure 11:
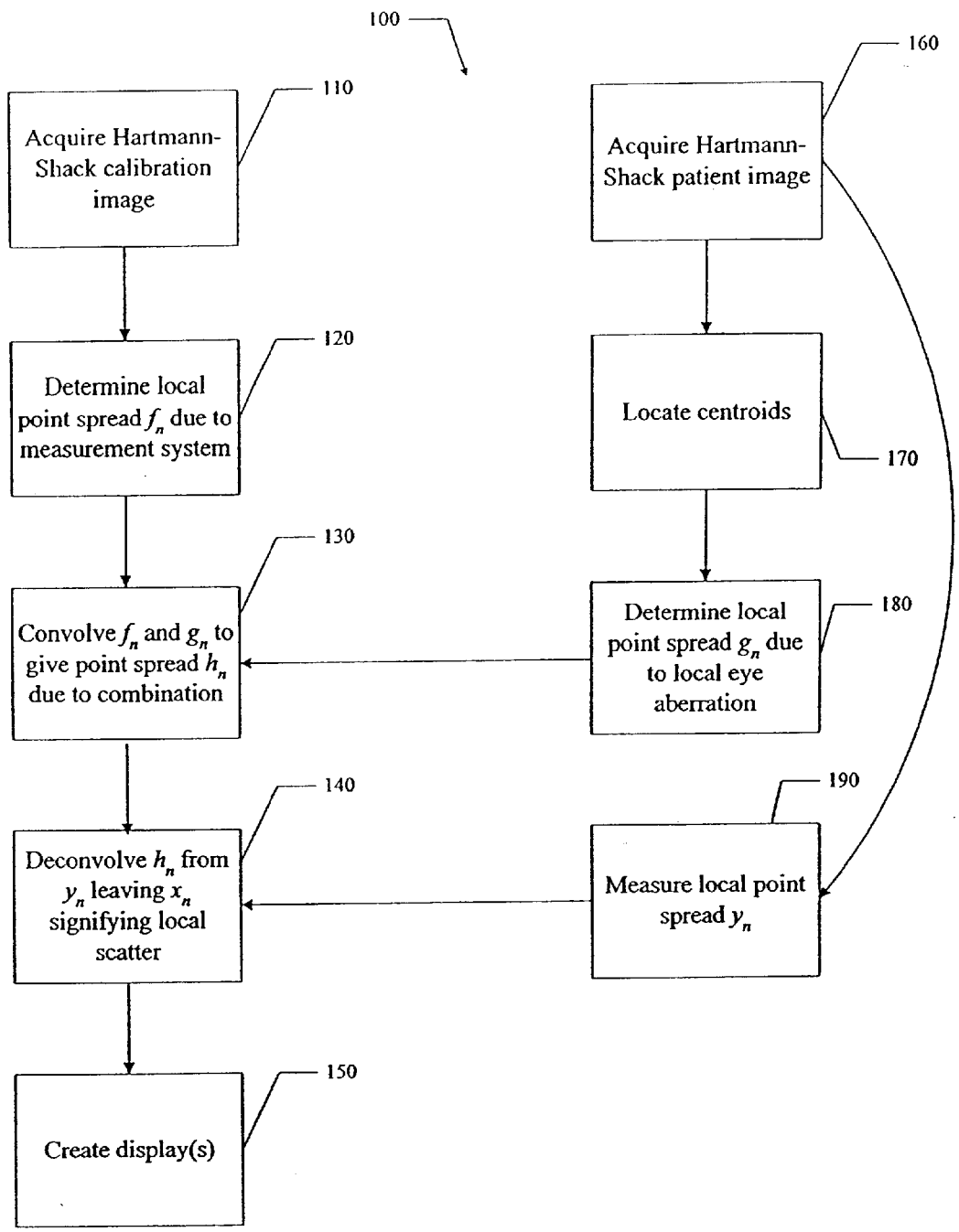
FIG. 11 is another flow chart illustrating a method for measuring local scattering of an optical medium according to the present disclosure.

FIGS. 10–11 summarize the methodology described above in process-flow fashion. FIG. 10 shows a general method 10 for measuring scatter as described above. In step 30, an image is acquired. This image may be acquired via film or digitally via a CCD device or the like. The image may be acquired using a Hartmann-Shack wavefront sensor or any other device suitable for subdividing light exiting from a target so as to generate a spatially-resolved image. In step 40, centroids of spots within the image are located. Any one of several centroid-locating algorithms known in the art may be used in this step. In step 50, gross aberrations are removed from the image. By this step, it is meant that one may determine aberrations due to the measurement system itself and due to local aberrations of the target. Such aberrations may be determined by methods known in the art by noting the geometrical shift in image spots within the image array relative to images within a calibration image array (which may be formed by imaging a plane wave). These shifts are measured relative to the centroids determined in step 40. In step 60, the amount of scatter within individual lenslet images is calculated. In one embodiment, this calculation may be achieved using the steps, or steps similar thereto, outlined above. The amount of spread of each corrected spot (each spot with non-scattering components removed) may be computed by a variety of possible methods (e.g. standard deviation, equivalent width, half width at half height, autocorrelation width, mean square width). Given these measures of spread at different positions in the eye's exit pupil, a smooth function depicting the spatial pattern of scatter may be computed by standard interpolation algorithms.

FIG. 11 shows a more detailed method 100 for measuring scatter in accordance with the present disclosure. In step 110, a Hartmann-Shack measurement system calibration image is acquired. The calibration image may be formed by imputting a plane wave into the system using, for instance, a precision collimator. In step 120, the local point spread $f_n$ due to the measurement system is determined, as is known in the art.

As described below, displacement of individual centroids from the optical axes of the corresponding lenslets is used to compute the wavefront aberration function of the measurement system. This function is then truncated to the dimensions of any given sub-aperture and used to construct a pupil function, from which the local point spread of an individual lenslet is computed using the Fourier transform as described above.

In step 160 of FIG. 11, a Hartmann-Shack image of a patient's eye is acquired (in other embodiments, the subject may be an inanimate object such as an optical device). In step 170, centroids of individual lenslet images are determined, and those centroids particularly, the shifts of those centroids relative to the calibration image) are used to determine local point spread $g_n$ due to local eye aberration (s). In step 130, $f_n$ and $g_n$ are convolved (see Equation (1)) to give point spread $h_n$. Point spread $h_n$ is attributable to both measurement system aberrations and local eye (or object under study) aberrations.

Figure 12:
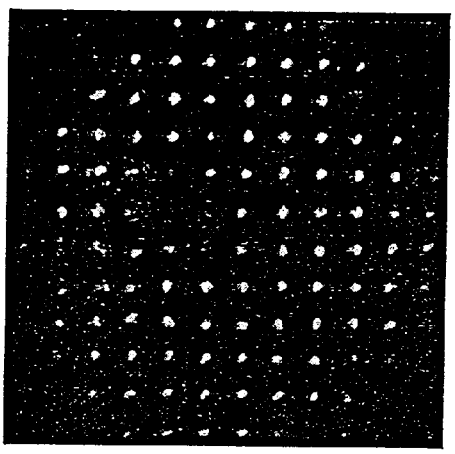
FIGS. 12 and 13 illustrate the generation of a scatter map.
Figure 13:
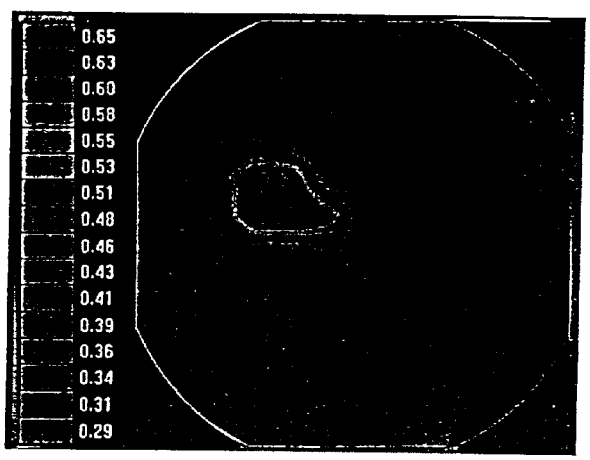

In step 190, the point spread function of each individual lenslet image from the patient image is measured here denoted as $y_n$. In step 140, $h_n$ is deconvolved from $y_n$ to leave $x_n$, which signifies the component of the patient image due to scatter. This deconvolution process may be carried forth using mathematical techniques such as Equations (2)–(4). In step 150, the quantitative value for the component due to scattering may be plotted to create one or more scattering maps. A scattering map, and the Hartmann-Shack image upon which it was based, are shown in FIGS. 12–13. Easy visualization of the variation of scatter across the pupil (see FIG. 13) may be performed using a bilinear interpolation of the local scatter data and standard color mapping methods. Using different colors, one may use "hot" colors to correspond to regions of greater scatter (lenslet point spread large) and "cool" colors to correspond to regions where there is less scatter (lenslet point spread narrow). Maps such as those shown in FIG. 13 may be used to identify and localize the source of scatter, such as a cataract or corneal scar.

Figure 14:
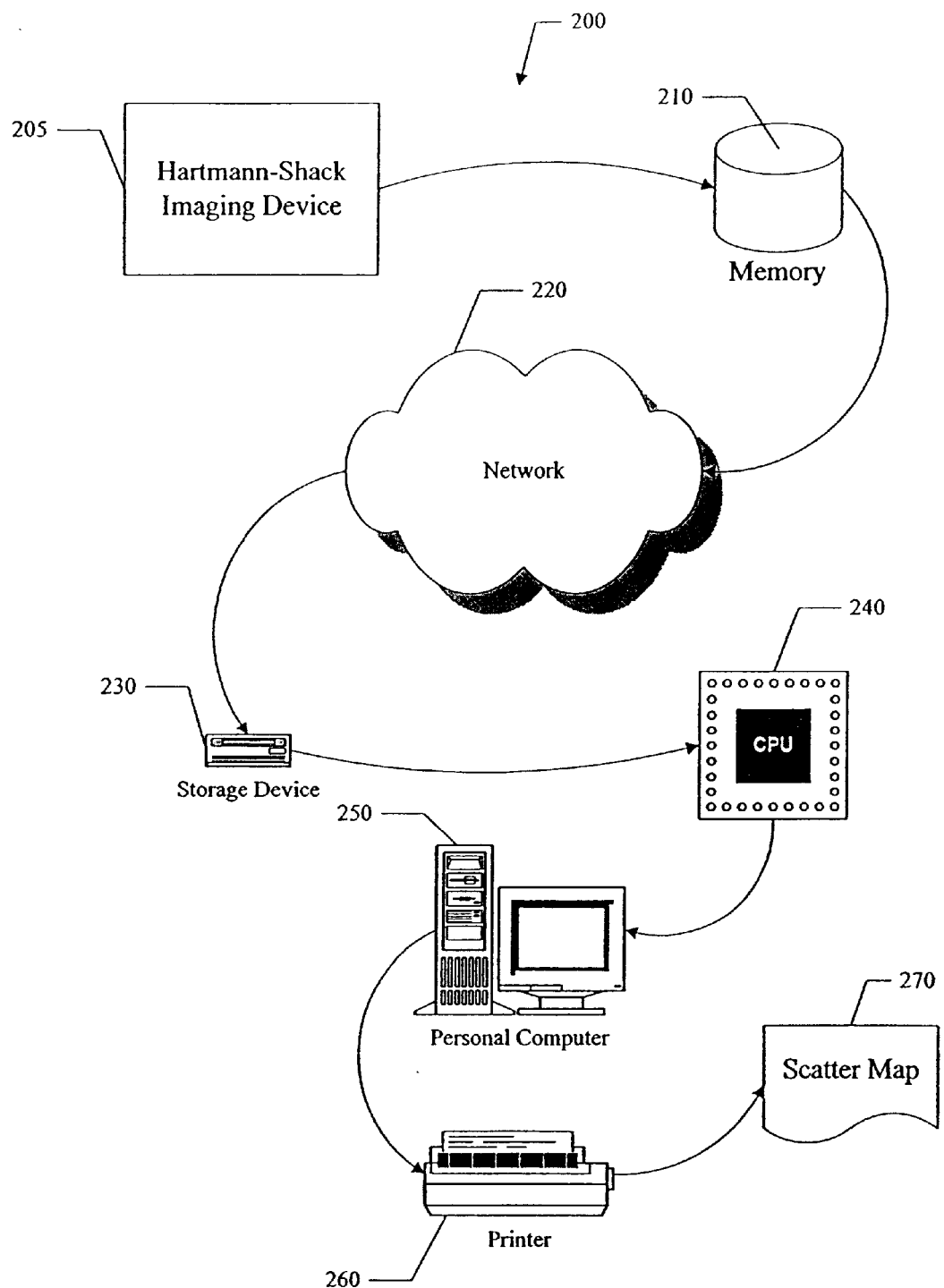
FIG. 14 shows a system for measuring local scattering according to the present disclosure.

Turning to FIG. 14, there is shown a system 200 suitable for generating a scatter map 270 in accordance with the present invention. In the illustrated embodiment, the system includes a Hartmann-Shack wavefront sensor 205, a memory 210, a network 220, a storage device 230, a microprocessor 240, a personal computer 250, a printer 260, and a hard-copy scatter map 270.

Hartmann-Shack wavefront sensor 205 is configured to obtain spatially-resolved images of an optical medium subject. Suitable devices are varied and include systems such as those depicted in FIGS. 2–4 and those disclosed in U.S. Pat. No. 5,777,719, which has been incorporated by reference.

Memory 210 may be configured to store information corresponding to the images formed of the subject by the Hartmann-Shack wavefront sensor 205. In one embodiment, memory 210 may be integrated with Hartmann-Shack wavefront sensor 205. Any device suitable for storing data, permanently or temporarily, may be used as memory 210. For instance, random access memory, a hard drive, a tape drive, an optical drive or the like may be used. In one embodiment, a separate memory 210 may not be needed. In such an embodiment, Hartmann-Shack wavefront sensor 205 may directly transfer information to a device suitable for making one or more calculations on-the-fly, without need for specific storage of that information.

Shown in FIG. 14 is network 220. Network 220 is illustrated to emphasize that Hartmann-Shack wavefront sensor 205 and memory 210 may be remotely connected to a calculation device, such as personal computer 250. In fact, Hartmann-Shack wavefront sensor 205 and memory 210 (or any equipment that may transfer information) may be remotely connected through a network or other suitable means. Network 220 may be any one of various types of networks. In one embodiment, network 220 may be the Internet. In other embodiments, network 220 may be a Local Area Network (LAN), a Wide Area Network (WAN), an intranet, or the like. In one embodiment, network 220 may not be needed. In such an embodiment, one or more pieces of equipment may be coupled directly.

Storage device 230 illustrates that system 200 may employ more than one memory for the storage of information. In the illustrated embodiment, information from Hartmann-Shack wavefront sensor 205 may be transferred to memory 210. The information may then be transferred over network 220 to storage device 230 so that a calculation device, such as personal computer 250, may access that information. In one embodiment, storage device 230 may be an external hard drive. In another embodiment, storage device 230 may be an internal hard drive of personal computer 250. In yet other embodiments, storage device 230 may be random access memory, an optical drive, a tape drive, a floppy drive, or the like. In one embodiment, storage device 230 may not be needed. In such an embodiment, information may be transferred from Hartmann-Shack wavefront sensor 205 directly to personal computer 250, or it may be transferred from Hartmann-Shack wavefront sensor 205 to memory 210 to personal computer 250.

Microprocessor 240 is configured to perform the instructions disclosed herein to convert information from Hartmann-Shack wavefront sensor 205 into map 270. Specifically, microprocessor 240 may be configured to perform instructions (via software) for measuring a point spread function of an image of the medium; for determining a component due to optical aberration; and for calculating the component due to scatter to measure the local scattering. More generally, microprocessor 240 may be instructed to perform any one or combination of operations discussed throughout this description. In the illustrated embodiment, microprocessor 240 is the Central Processing Unit (CPU) of personal computer 250. In other embodiments, microprocessor 240 may be the processing unit of any number of other calculating devices, such as but not limited to, a hand-held computer, a laptop computer, a personal digital assistant, or the like.

Again, software suitable to provide instructions to microprocessor 240 may be used. Specifically software may be used to perform any one or combination of steps described throughout this specification. With the benefit of the present disclosure, and especially the equations contained herein, one of skill in the art may implement suitable software in one of many different ways. In one embodiment, a program may be written in a language such as C++, Fortran, or Visual Basic. In other embodiments, a language specifically designed to interface with Hartmann-Shack wavefront sensor 205 may be utilized. In still other embodiments, commercially available math processing software such as MATHEMATICA and/or MatLab may be instructed to carry out any one or combination of instructions disclosed in this specification. In one embodiment, image processing software may be written in C or C++ as separate modules to an existing software package to display map 270. The maps may be displayed in any arbitrary orientations and view angles, as is known in the art.

Printer 260 is illustrated in FIG. 14 to demonstrate that map 270 may be presented in various forms. It may be printed, viewed directly on a monitor, viewed as a movie, or by any other means suitable to convey the scattering information to a user.

To estimate the importance of deconvolution, the inventors have performed a series of controlled simulations introducing small to large amounts of local aberration over a lenslet. Controlled simulations for these estimates were chosen because in a simulation, one may perfectly deconvolve x (scatter) as opposed to x' (a best estimate of scatter). This approach allowed the inventors to precisely determine the impact of varying amounts of local aberrations.

Figure 15:
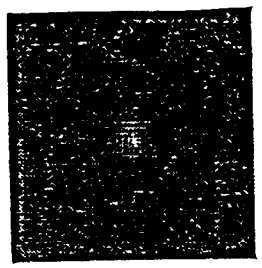
FIGS. 15–17 show outputs from a simulation performed in accordance with the present disclosure.
Figure 16:
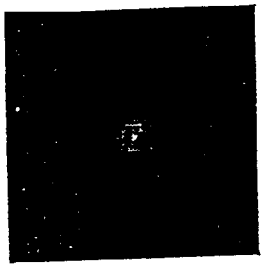
Figure 17:
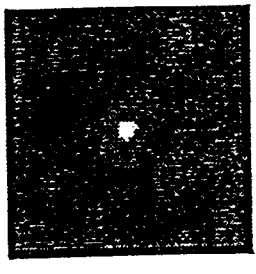

FIGS. 15–17 show outputs from one of the simulations, where y (FIG. 17) is a lenslet image, h (FIG. 16) is an aberrated point spread convolved with the instrument point spread, and x (FIG. 15) is a deconvolution of h from y. As the inventors had suspected, deconvolution seems to alter the estimate of scatter very little. The inventors' best estimate of the error induced by ignoring the local aberration was about 5% or less. Thus, even without correction for local aberrations, variation of the point spread between lenslets is by itself a good estimate of local scatter within the optical system of interest.

As mentioned previously, the methodology disclosed herein may be used to measure not only scatter, but also local absorption of media, including the eye. The measure of absorption may then be used to identify (and, subsequently, correct) sources of ocular absorption such as cataracts, etc. The total amount of light captured by each lenslet in a Hartmann-Shack image depends on the product of two factors: (1) the reflectivity of the fundus in the direction of the lenslet, and (2) the optical transmission of the ocular media in the same direction. Factor (1) may be measured, as is known in the art, by a calibration measurement. For measurements with the eye, factor (1) may be estimated independently by a behavioral experiment in which visual sensitivity is measured at different pupil locations as is known in the art. The resulting description of how sensitivity varies with pupil location is known as the Stiles-Crawford function. This Stiles-Crawford function is due to the same visual mechanism (waveguide properties of photoreceptors) as factor (1), the directional reflectivity of the retina, and therefore is taken as a measure of factor (1). Thus, the unknown factor (2) may be determined by dividing physical measurements of integrated spot intensity by the Stiles-Crawford function. The result is interpreted as a measure of local absorption of the ocular media, which may be used to guide therapy for removing the source of ocular absorption (e.g. cataract, corneal scar, etc.).

All of the methods, systems, and apparatus disclosed and claimed herein can be made and executed without undue experimentation in light of the present disclosure. While the techniques of this invention have been described in terms of specific embodiments, it will be apparent to those of skill in the art that variations may be applied to the disclosed methodologies and in the steps of the method described herein without departing from the concept, spirit and scope of the invention.

REFERENCES

The following references, to the extent that they provide exemplary procedural or other details supplementary to those set forth herein, are specifically incorporated herein by reference.

1. Liang, Grimm, Goelz, and Bille, "Objective measurement of wave aberrations of the human eye with the use of a Hartmann-Shack wave-front sensor," J. Opt. Soc. Am. A., vol. 11, no. 7, pages 1949–1957, July 1994.
2. Liang, Williams, and Miller, "Supernormal vision and high-resolution retinal imaging through adaptive optics," J. Opt. Soc. Am. A., vol. 14, no. 11, pages 2884–2892, November 1997.

3. Salmon, Thibos, and Bradley, "Comparison of the eye's wave-front aberration measured psychophysically and with the Shack-Hartmann wave-front sensor," J. Opt. Soc. Am. A., vol. 15, no. 9, pages 2457–2465, September 1998.
4. Roorda and Williams, "The arrangement of the three cone classes in the living human eye," Nature, vol. 397, pages 520–522, Feb. 11, 1999.
5. U.S. Pat. No. 5,777,719.
6. Smith, Modern Optical Engineering, Second Edition, McGraw-Hill, 1990, Chapter 11.
7. Gaskill, J. D. (1978), Linear Systems, Fourier Transforms, and optics, New York, John Wiley & Sons.
8. Pratt, Digital Image Processing, Second Edition, Wiley Interscience, 1991, Chapter 12.
9. Gonzalez and Woods, Digital Image Processing, Addison Wesley, 1992.
10. Russ, The Image Processing Handbook, second edition, CRC Press, 1994.

What is claimed is:

1. A method for measuring scattering of an optical medium, comprising:

acquiring a plurality of point spread functions of the medium, each point spread function comprising a component due to optical aberration of the medium and a component due to scatter;

determining the component due to optical aberration;

determining the component due to scatter; and localizing the scattering of the optical medium.

2. The method of claim 1, wherein the acquiring comprises acquiring a Hartmann-Shack image.

3. The method of claim 1, further comprising generating a display of the scattering of the medium.

4. The method of claim 1, wherein the medium comprises an eye.

5. The method of claim 4, further comprising identifying a defect of the eye using the component due to scatter, the defect contributing to local scattering.

6. The method of claim 5, wherein the defect comprises a cataract.

7. The method of claim 5, wherein the defect comprises an abnormality of a tear film, a corneal scar, a vacuole, edema, a foreign body, an abnormality of a lens, an abnormality of the vitreous, drusen, defective contact lenses, defective spectacle lenses, intraocular lens, or any combination thereof.

8. claim The method of claim 5, further comprising treating the defect.

9. The method of claim 5, wherein the identifying a defect comprises identifying a defect before or after laser eye surgery.

10. A method for displaying scattering characteristics of an optical medium, comprising:

acquiring a Hartmann-Shack calibration image of a measurement system to define a first plurality of point spread functions;

acquiring a Hartmann-Shack test image of the medium to define a second plurality of point spread functions;

determining a shift between the test image and the calibration image;

measuring a point spread of each of the second plurality of point spread functions, each of second plurality of point spread functions comprising a component due to optical aberration of the medium and a component due to scatter;

determining the component due to optical aberration using the shift;

deconvolving the component due to optical aberration to determine the component due to scatter;

localizing the scattering characteristics of the optical medium; and generating a display of the localized scattering characteristics using the component due to scatter.

11. The method of claim 10, wherein the medium comprises an eye.

12. The method of claim 11, further comprising identifying a defect of the eye using the component due to scatter, the defect contributing to local scattering.

13. The method of claim 12, wherein the defect comprises a cataract.

14. The method of claim 12, wherein the defect comprises an abnormality of a tear film, a corneal scar, a vacuole, edema, a foreign body, an abnormality of a lens, an abnormality of the vitreous, drusen, defective contact lenses, defective spectacle lenses, intraocular lens, or any combination thereof.

15. The method of claim 12, further comprising treating the defect.

16. The method of claim 12, wherein the identifying a defect comprises identifying a defect before or after laser eye surgery.

17. A method for identifying a defect of an eye, the method comprising:

acquiring a plurality of point spread functions of the eye, each point spread function comprising a component due to optical aberration of the medium and a component due to scatter;

determining the component due to optical aberration;

determining the component due to scatter;

localizing scattering of the eye; and identifying the defect using the component due to scatter.

18. The method of claim 17, further comprising treating the defect.

19. A method for identifying a defect of an eye, comprising:

acquiring a Hartmann-Shack calibration image of a measurement system to define a first plurality of point spread functions;

acquiring a Hartmann-Shack image of the eye to define a second plurality of point spread functions;

determining a shift between the image of the eye and the calibration image;

measuring a point spread of each of the second plurality of point spread functions, each of second plurality of point spread functions comprising a component due to optical aberration of the medium and a component due to scatter;

determining the component due to optical aberration using the shift;

deconvolving the component due to optical aberration to determine the component due to scatter; and localizing scattering of the eye; and identifying the defect using the component due to scatter.

20. The method of claim 19, further comprising treating the defect.

* * * * *

UNITED STATES PATENT AND TRADEMARK OFFICE
CERTIFICATE OF CORRECTION

PATENT NO.    : 6,659,613 B2
DATED         : December 9, 2003
INVENTOR(S)   : Applegate et al.

It is certified that error appears in the above-identified patent and that said Letters Patent is hereby corrected as shown below:

<u>Column 15,</u>
Line 47, delete "claim" before "The".

<u>Column 16,</u>
Line 59, delete "and" after "due to scatter;".

Signed and Sealed this

Sixteenth Day of March, 2004

JON W. DUDAS
*Acting Director of the United States Patent and Trademark Office*